United States Patent [19]

Flynn et al.

[11] Patent Number: 5,421,327
[45] Date of Patent: Jun. 6, 1995

[54] BITE BLOCK HAVING FINGER-ACCOMMODATING OPENINGS

[75] Inventors: Mary E. Flynn, 936 Pinellas Bayway, Unit 5, Tierra Verde, Fla. 33715; Neil T. Flynn, St. Petersburg, Fla.

[73] Assignee: Mary E. Flynn, Tierra Verde, Fla.

[21] Appl. No.: 73,021

[22] Filed: Jun. 7, 1993

Related U.S. Application Data

[63] Continuation-in-part of Ser. No. 918,501, Jul. 22, 1992, abandoned.

[51] Int. Cl.$^6$ .................. A61M 16/00; A62B 9/06
[52] U.S. Cl. .................. 128/207.17; 128/200.26; 128/DIG. 26; 128/912
[58] Field of Search ............ 128/200.26, 207.14, 128/207.17, 912, DIG. 26

[56] References Cited

U.S. PATENT DOCUMENTS

| | | | |
|---|---|---|---|
| 4,235,229 | 11/1980 | Ranford et al. | 128/DIG. 26 |
| 4,331,144 | 5/1982 | Wapner | 128/DIG. 26 |
| 4,622,968 | 11/1986 | Persson | 128/200.26 |
| 4,944,313 | 7/1990 | Katz et al. | 128/207.14 |
| 5,273,032 | 12/1993 | Borody | 128/207.14 |

*Primary Examiner*—Kimberly L. Asher
*Attorney, Agent, or Firm*—Joseph C. Mason, Jr.; Ronald E. Smith

[57] ABSTRACT

A bite block where, in a first embodiment, the mouthpiece is flanked by laterally-extending arms that define large, inverted "U"-shaped finger-accommodating openings so that a surgeon may guide a surgical tool by placing fingers within those openings. The mouthpiece has a cylindrical throughbore that receives the surgical instrument. The upper and lower teeth of the patient are supported by flat upper and lower support walls that are formed integrally with the mouthpiece, and each support wall includes a retention ridge that helps keep the mouthpiece in the patient's mouth. Upper and lower flanges extend above and below the plane of their respective support walls, so that the mouthpiece cannot enter the patient's mouth even when the surgeon pulls back the patient's lips to their limit. In a second embodiment, the arms are eliminated to provide unlimited finger access, and a strap has a bifurcated section so that it can weave through upper and lower parts of the bite block to provide a fastener that ensures at least one of its ends will be accessible even when a patient's head is turned to the side on a pillow. In both embodiments, a cushioned pad overlies the mouthpiece for the comfort of edentulous patients.

5 Claims, 4 Drawing Sheets

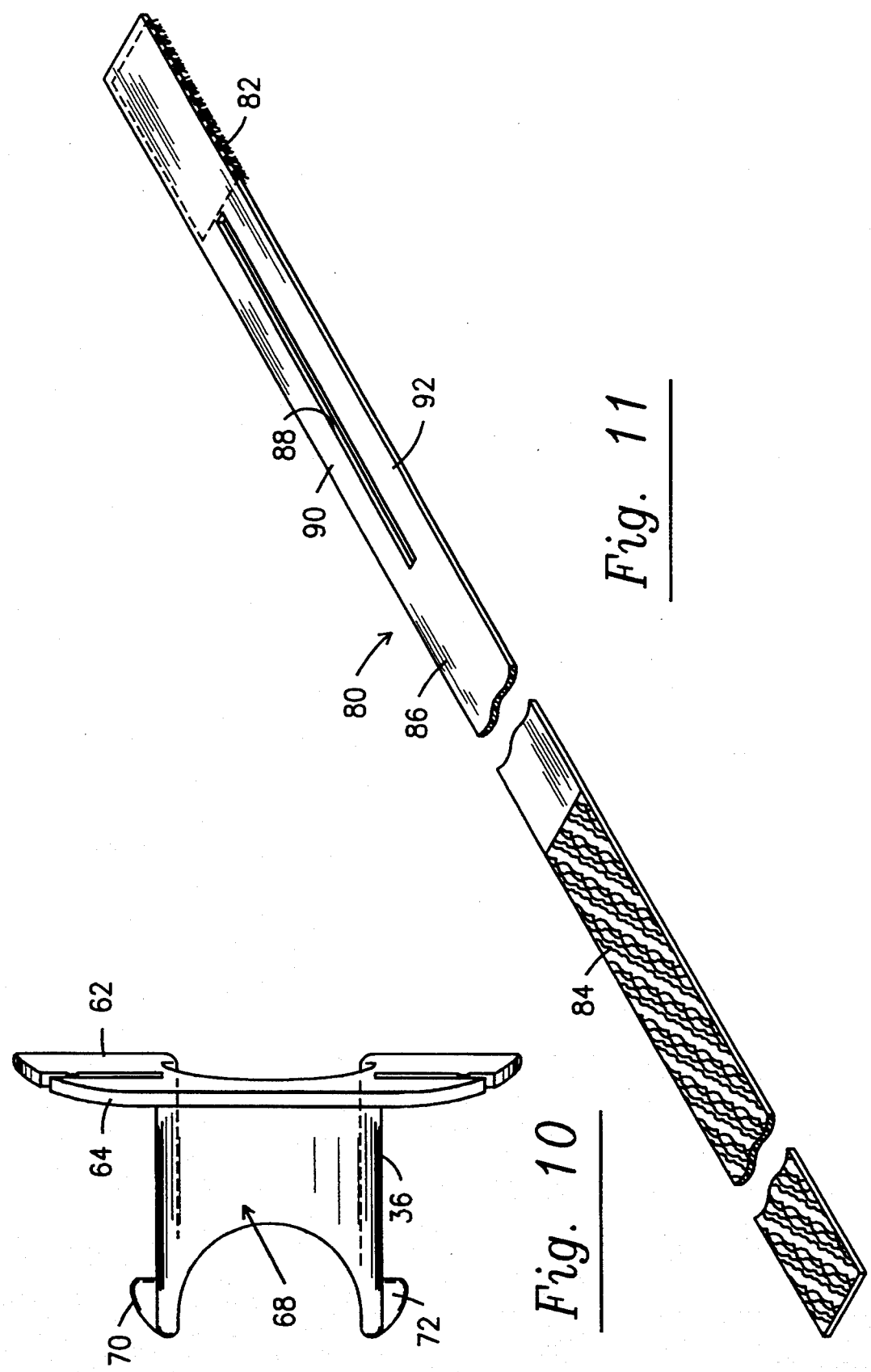

BITE BLOCK HAVING FINGER-ACCOMMODATING OPENINGS

CROSS-REFERENCE TO RELATED DISCLOSURE

This disclosure is a continuation-in-part of a disclosure filed Jul. 22, 1992 bearing Ser. No. 07/918,501, now abandoned, by the same inventors, entitled "Bite Block Having Finger-Accommodating Openings."

BACKGROUND OF THE INVENTION

1. Field of the Invention

This invention relates, generally, to bite blocks. More particularly, it relates to a bite block having enhanced utility because it accommodates the fingers of the physician and certain medical instruments.

2. Description of the Prior Art

Bite blocks are used to hold open the mouth of a patient when an endoscope or other surgical instrument is inserted down the patient's throat and into his or her stomach or intestines, for example. Typically, bite blocks include a hollow mouthpiece upon which the patient bites when the mouthpiece part of the bite block is inserted into the patient's mouth. A flange surrounds the mouthpiece and, theoretically at least, insures that only the mouthpiece itself will enter the patient's mouth, i.e., the flange overlies the patient's lips and is intended to be too large to enter the patient's mouth; thus, it serves as a retainer for the hollow mouthpiece. The hollow mouthpiece defines a tunnel or bore through which the surgical instrument is inserted. For example, a surgical instrument such as an endoscope, as aforesaid, may be inserted through the bore defined by the mouthpiece. Without the bite block, a sleeping patient might involuntarily or reflexively bite down on the endoscope or other device and injure his or her teeth; a fully awake patient might also do the same.

Insertion of the surgical instrument is somewhat problematical; most physicians like to guide the instrument down the patient's throat with their fingers, but often the bite block itself interferes with such finger utilization. In all of the known bite block designs, the opening in the hollow mouthpiece is too small to accommodate one or more surgical instruments and one or more fingers at the same time. If the physician pulls the patient's lips back in an effort to get around the flange that surrounds the mouthpiece, a risk is created that the bite block could fully enter into the patient's mouth since such pulling back on the lips defeats the purpose of the flange. Since bite blocks are usually made with a hard plastic material, such unintentional insertion could result in trauma to the patient's mouth.

Numerous bite block designs have been patented over the years, but an effective bite block that allows the physician to guide the instrument into position with ease has heretofore eluded inventors. For example, U.S. design U.S. Pat. No. 283,158 to Jackson shows an endoscopic bite block that includes a strap for holding the bite block in position. It also includes what are apparently material-saving openings formed in the flange on opposite ends of the mouthpiece, but those openings are of inadequate size to accommodate fingers. The mouthpiece of the Jackson device is elliptical in shape, apparently because that is the general shape of a slightly opened mouth, and because an ellipse provides a reasonably flat surface to support both the patient's upper and lower teeth.

Another U.S. design patent of interest is U.S. Pat. No. 297,665. U.S. utility patents of interest include U.S. Pat. Nos. 4,249,529, 4,744,358, 4,425,911, 4,867,154, 3,422,817, 4,502,478, 4,986,815, 4,191,180, and 4,732,147.

The known bite blocks cannot accommodate certain medical instruments because their openings are too small. For example, no bite block heretofore known can accommodate a #60F bougie dilator.

Another shortcoming of known bite blocks arises from the way they are held onto a patient's head. Typically, the bite block is held into position by an elongate strap; a first end of the strap engages a first end of the bite block, the medial part of the strap extends around the back of the patient's head, and a second end of the strap engages a second end of the bite block. Thus, one end of the strap will almost always lie under a patient's head when the patient's head is resting on a pillow; thus, the health care provider must move the patient's head to attach the strap to the bite block.

The ideal bite block would allow the physician's fingers to guide the instrument without restriction, and would not fall into the patient's mouth even when the patient's lips were pulled back to their limit. It would also have an instrument insertion opening of round configuration to better accommodate instruments of the type inserted through the access opening of a bite block, but would provide upper and lower flat surfaces for supporting the patient's upper and lower teeth, respectively. Moreover, it would also allow insertion of a dilator up to #60F. The ideal bite block would also be very comfortable for the patient, and would be designed so that the health care provider would not need to move the patient's head to secure the strap. However, the prior art, considered as a whole as required by law, neither taught nor suggested to those of ordinary skill in the art of bite block design, at the time the present invention was made, how the ideal bite block could be created.

SUMMARY OF THE INVENTION

The longstanding but heretofore unfulfilled need for an improved bite block is now fulfilled. The novel bite block has a cylindrical mouthpiece and thus a cylindrical access opening to better accommodate the instruments inserted through it, yet provides flat surfaces upon which the patient's teeth may bite. Just as importantly, the novel design allows the physician to easily insert his or her fingers into the patient's mouth to guide the instrument or instruments being inserted through the access opening. In a first embodiment, this feature is provided by uniquely designed arms and flanges that prevent the bite block from entering the patient's mouth even when the patient's lips are pulled back to their limit yet which accommodates the physician's fingers.

In the first embodiment, auxiliary means are provided for retaining the mouthpiece within the patient's mouth; said auxiliary means complement the strap that engages opposite ends of the bite block arms and which wraps around the back of the patient's head.

In a second embodiment, the flanges are still provided to prevent the mouthpiece from entering the patient's mouth, but the arms are eliminated so that the physician's fingers have unlimited space available for instrument manipulation.

In the second embodiment, a unique strap is also employed. It is constructed such that it may be tightened in the absence of need to move the patient's head even when the patient's head is supported by a pillow. The strap is preferably constructed of an elastomeric, stretchable material. Importantly, it is easy to operate, even with a gloved hand.

In both embodiments, the flanges also serve to keep the bite block in its proper position, and an optional, cushioned pad is slippable onto the mouthpiece to enhance the comfort of patients having no or few teeth. Both the bite block and the pad are disposable to prevent the spread of communicable diseases.

Thus it is understood that the primary object of this invention is to provide a bite block that enables a physician to use his or her fingers when inserting a surgical instrument into a patient's body through the patient's mouth.

Another important object is to provide a bite block that does not enter the patient's mouth even when the patient's lips are pulled back tightly.

Still another object is to provide a bite block that better accommodates cylindrical instruments through the mouthpiece opening, yet which provides flat surfaces upon which the patient's teeth may bite.

Another object is to allow insertion of a dilator #60F and above that prior art bite block designs do not accept.

It is also an object of this invention to provide the first bite block, of the type including a head strap, that provides unlimited finger access.

These and other important objects, features and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which:

FIG. 10 is a side elevational view thereof; and

FIG. 11 is a perspective view of the novel strap of the second embodiment.

Similar reference numerals refer to similar parts throughout the several views of the drawings.

DETAILED DESCRIPTION OF THE PREFERRED EMBODIMENT

Figure 1:
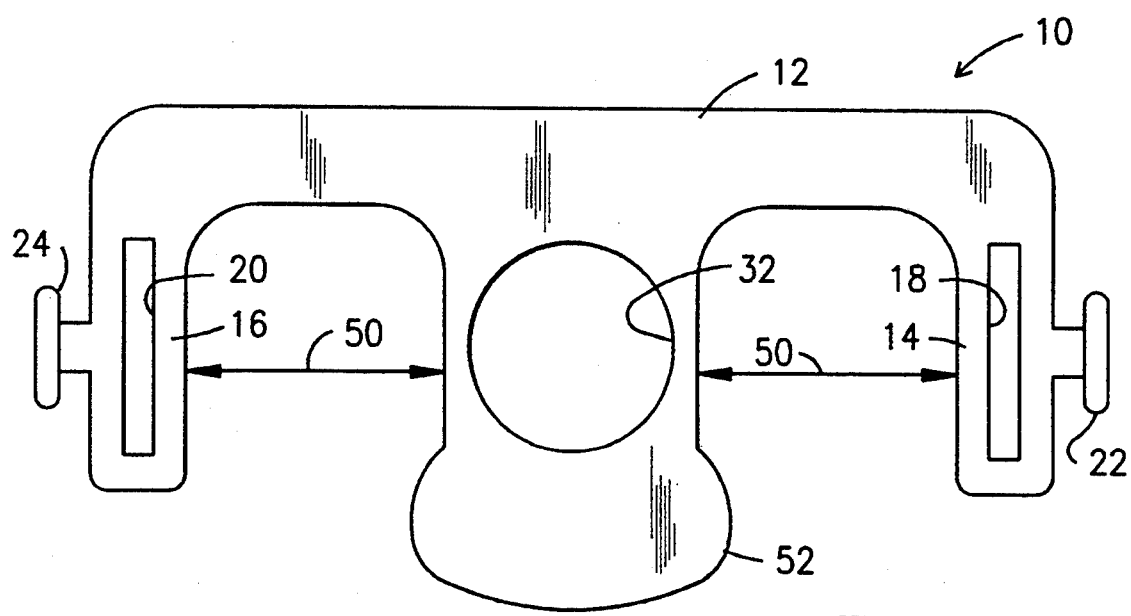
FIG. 1 is a front elevational view of a first illustrative embodiment of the invention.

Referring now to FIGS. 1-4, it will there be seen that a first exemplary embodiment of the invention is denoted as a whole by the reference numeral 10.

Figure 2:
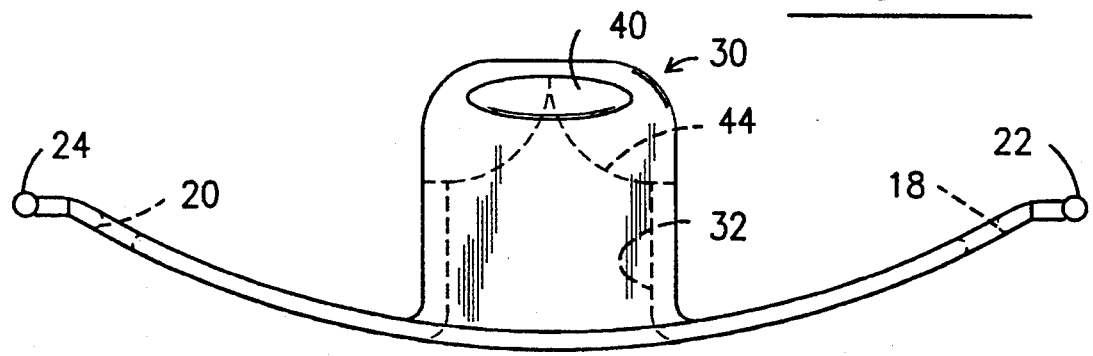
FIG. 2 is a top plan view thereof.

Bite block 10 includes a flat, laterally extending, arcuate upper flange 12 and a pair of depending arms 14, 16 integrally formed therewith at opposite ends thereof. The curvature of flange 12 is best shown in FIG. 2; said curvature follows the contour of the patient's face. Vertically oriented slots 18, 20 are formed in arms 14, 16, respectively, and provide mounting means for opposite ends of a conventional strap, not shown, that wraps around the back of the patient's head when the bite block is in use to prevent it from leaving the patient's mouth.

Figure 5:
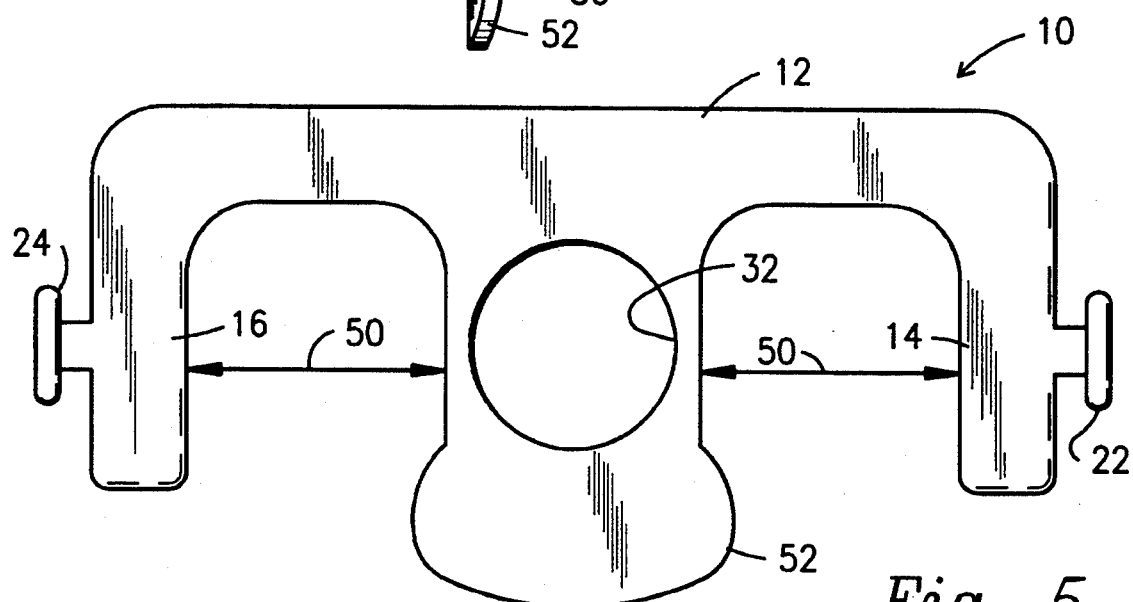
FIG. 5 is a front elevational view of a minor variation to the first embodiment.

In a variation of the first embodiment, shown in FIG. 5, slots 18, 20 are not used because the strap simply loops around each arm 14, 16.

"T"-shaped tabs 22, 24 extend laterally from arms 14, 16, respectively, and provide means for further retention of the conventional strap. More particularly, the strap has a small slot formed therein near each of its opposite ends, and such slots receive the tabs 22, 24 and thus engage the strap to ensure that it does not slip from the arms 14, 16.

Figure 4:
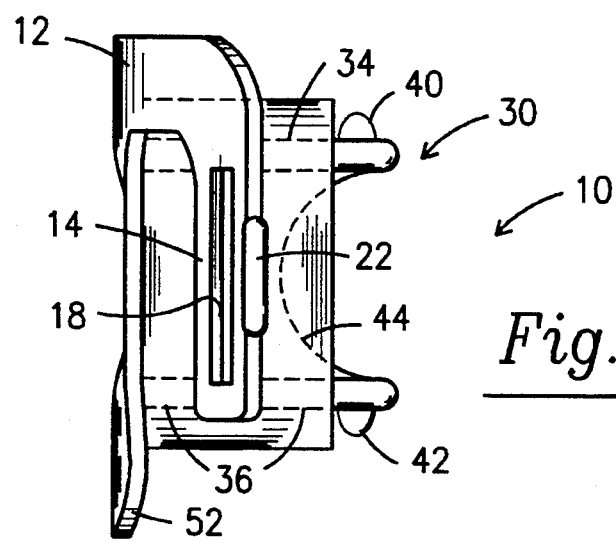
FIG. 4 is a side elevational view thereof.

Reference numeral 30 denotes the mouthpiece part of the bite block as a whole. Mouthpiece 30 is integral with flange 12 and extends therefrom about mid-length thereof. Unlike upper flange 12 and arms 14, 16, mouthpiece 30 is not flat; as shown in FIGS. 2 and 4, it extends rearwardly so that it extends into a patient's mouth when the bite block 10 is in use. A cylindrical throughbore 32 is formed in mouthpiece 30; said throughbore has a circular appearance when viewed frontally, as depicted in FIG. 1. The surgical instruments employed by the surgeon are inserted through this cylindrical opening 32; the circular configuration of the bore 32 matches the circular cross sectional structure of the surgical instruments inserted therethrough; this represents a more efficient use of space than the elliptical openings of the prior art.

Figure 3:
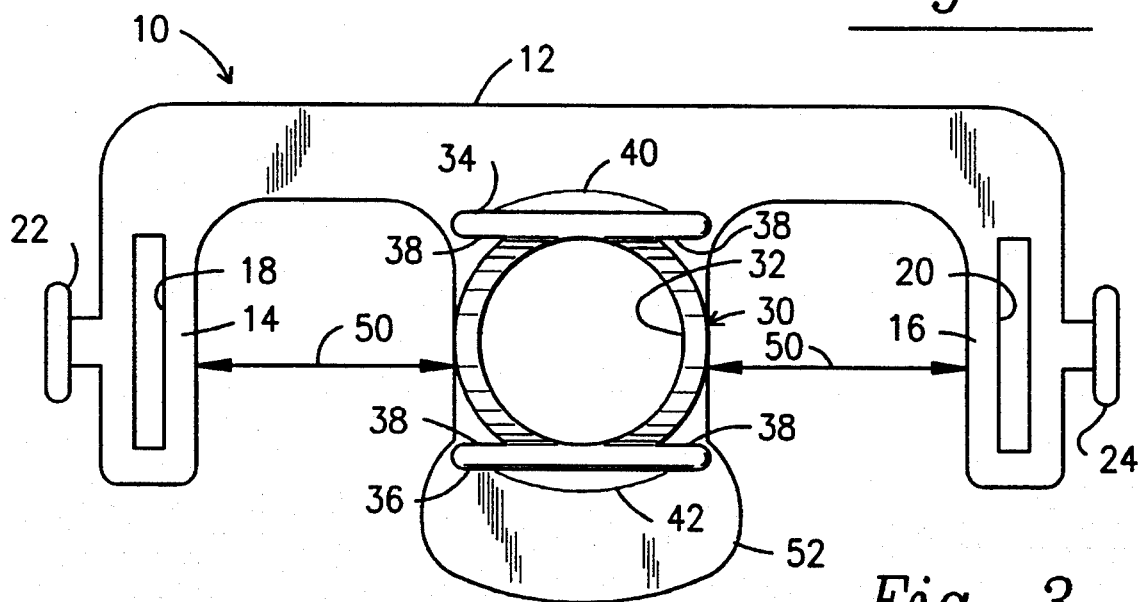
FIG. 3 is a rear elevational view thereof.
Figure 6:
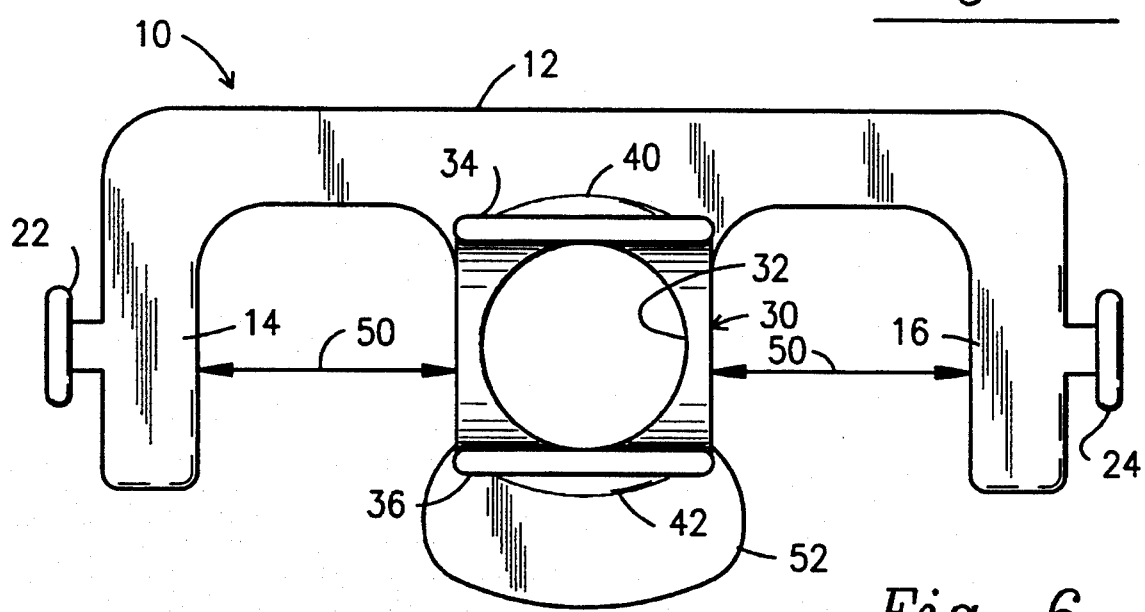
FIG. 6 is a rear elevational view of said minor embodiment.

However, it is important to provide a flat surface upon which the patient's teeth can rest; heretofore, cylindrical mouthpieces have been avoided for that very reason. The present invention retains the cylindrical aspect of the mouthpiece, yet provides a flat support surface for the teeth as well; this is accomplished by the provision of flat shelf members or tooth support walls 34, 36 (FIGS. 3 and 4). Upper support wall 34 is integral with cylindrical mouthpiece 30, as is lower support wall 36. In a variation of the first embodiment, FIG. 6, the four recesses or corners 38 formed by the merger of circular mouthpiece 30 and the flat support walls 34, 36 are eliminated; this embodiment uses more materials in fabrication than the first-depicted structure, but is easier to make and may be a little stronger.

A linear-in-configuration retention ridge 40 is integral with and projects a small distance upwardly from upper support wall 34, and a similar retention ridge 42 projects downwardly from lower support wall 36. Each ridge performs the function its name expresses, i.e., each ridge complements the function of the unillustrated strap and serves to retain the mouthpiece in the patient's mouth.

A finger access cut out 44 is formed in the cylindrical sidewalls of mouthpiece 30, as shown in FIGS. 2 and 4.

Perhaps the most important feature of this first embodiment is the large spacing between the mouthpiece 30 and the depending arms 14, 16; this spacing is denoted 50 in FIGS. 1 and 3. Spacing 50 accommodates a surgeon's fingers with room to spare and thus facilitates manipulation of the tool being inserted into the patient. Thus, unlike the bite blocks heretofore known, the novel bite block 10 presents no significant hindrances to the surgeon's task. Note that the space between the mouthpiece and each depending arm has the shape of an inverted "U" i.e., the space is open on the bottom; this affords still further spacing to accommodate the physician's fingers.

Moreover, the elongate extent of the depending arms 14, 16 ensure that bite block 10 will not enter the patient's mouth regardless of how far back the lips of the patient are pulled by the surgeon. Note further the lower flange 52 that is integral with and which depends from mouthpiece 30; it further serves to ensure that the bite block 10 will not enter the patient's mouth under those circumstances. Note the distance that said lower flange 52 extends below lower tooth support surface 36; the upper flange 12 projects upwardly above upper tooth support surface 34 by about the same amount, as clearly shown in FIG. 4, for the same reason. The depending arms 14, 16, have less vertical extent than the combined vertical extent of upper flange 12 and lower flange 52, as also shown in FIG. 4, but said arms 14, 16 are positioned at the opposite ends of the patient's mouth, where the distance between the upper and lower lips is less than the distance between said lips at the center where the mouthpiece 30 is.

Soft bite pad 31 (FIG. 4) is made of a stretchable and resilient sponge-like absorbent material. It may be slipped over mouthpiece 30 for the comfort of edentulous patients. It tightly conforms to the shape of mouthpiece 30 so that it will not slip off inadvertently.

A second embodiment of the novel bite block is depicted in FIGS. 7–11. In this embodiment, arms 14, 16 are eliminated so that the physician's finger access is completely unlimited. Thus, this second embodiment is believed to have more commercial potential than the first. More importantly, it is believed to be the first bite block, anywhere in the world, that is equipped with a head strap yet which provides unlimited finger access. (Earlier, strapless designs also provide unlimited access, but at the cost of losing the benefits gained by having a head strap).

The bite block of this second embodiment is denoted 60 as a whole. It includes base part 62, a pair of side parts, 64, 66, and mouthpiece 68.

Note that the base and side parts have a substantially common height almost double the extent of their collective width, and that the collective width of said three parts is substantially equal to the width of the mouthpiece 68. The height of said parts prevents the bite block 60 from entering the patient's mouth even when the patient's mouth is fully open and the patient's lips have been pulled out of the way by the physician or physician's assistant.

In FIG. 10 it can be seen that each tooth-retaining ridge 70, 72 has a leading edge that is ramped to facilitate sliding introduction of the mouthpiece over the patient's teeth; note that, unlike the corresponding parts of the first embodiment, each ridge extends to the leading end of the mouthpiece 68.

Figure 7:
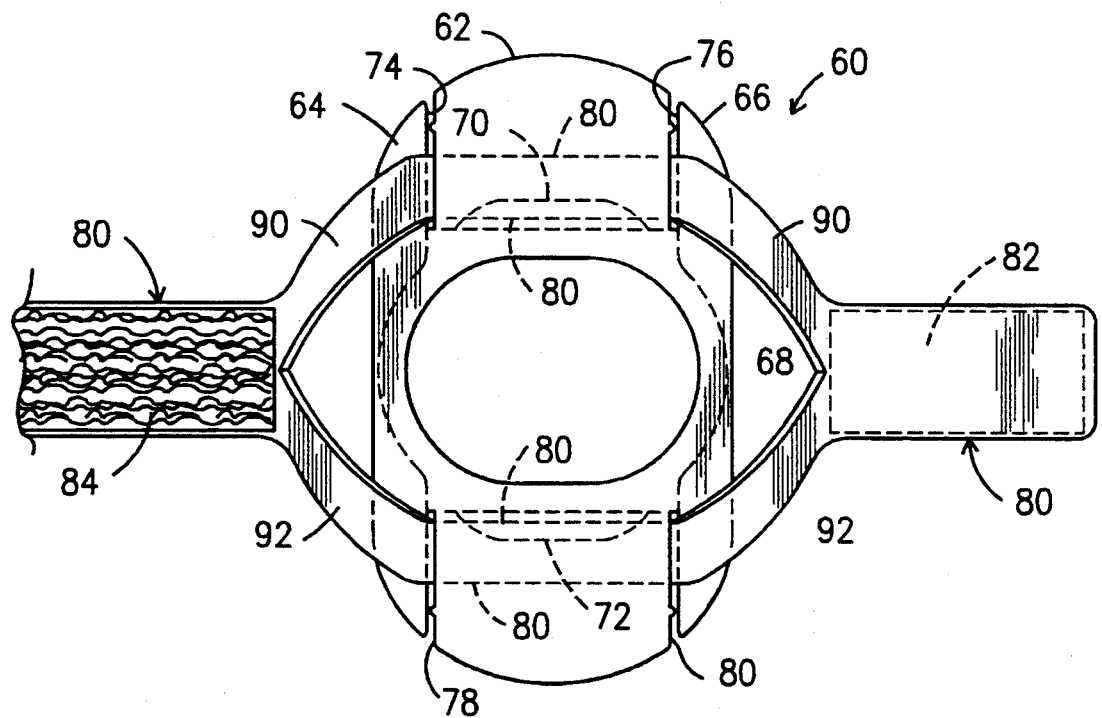
FIG. 7 is a front elevational view of a second illustrative embodiment.
Figure 8:
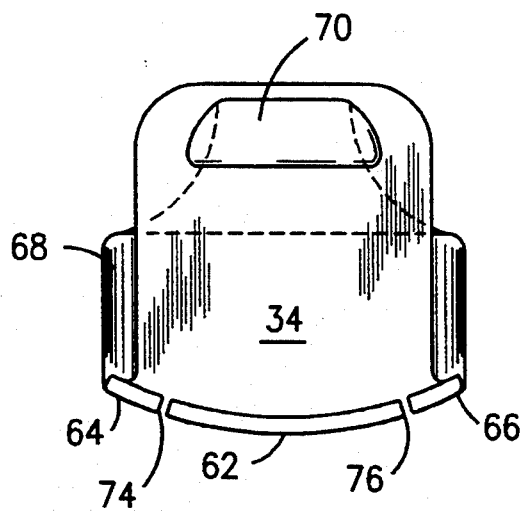
FIG. 8 is a top plan view thereof.

As perhaps best shown in FIG. 8, base part 62 and side parts 64, 66 are flat, gently curved pieces. As perhaps best understood in connection with FIGS. 8 and 10, the side parts are formed integrally with mouthpiece 68 and with base part 62, but are otherwise spaced apart from said base part by a predetermined distance. The spaces may be thought of as upper slots 74, 76, and lower slots 78, 80 (FIG. 7); each slot has a bottom represented by mouthpiece 68. Note strap retainers or lugs, collectively denoted 79 (FIG. 9), formed on opposite edges of the upper and lower parts of base part 62; these cooperate with mouthpiece 68 to perform the function of retaining strap 80 in position when the novel device is in use, i.e., they prevent the strap from riding out of its associated slot.

FIG. 7 shows how the strap is weaved through the upper and lower slots to hold the bite block 60 in position. The strap is shown extending laterally away from bite block 60; when said strap is attached to a patient, it extends into the plane of the paper.

Figure 9:
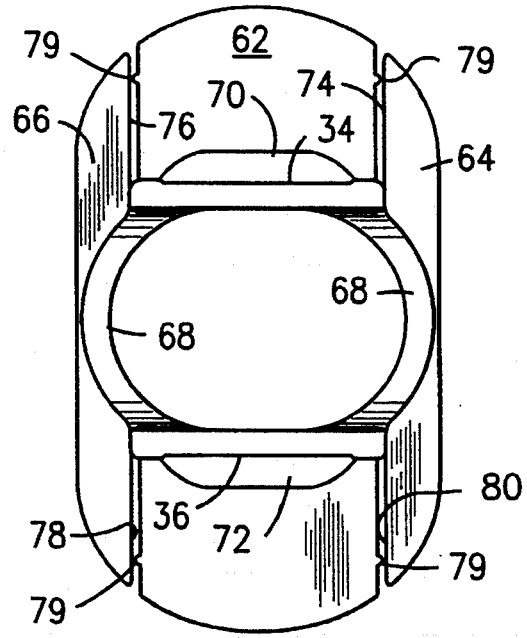
FIG. 9 is a rear elevational view thereof.

Strap 80, shown in perspective in FIG. 11, is also highly novel and has a number of advantages. It includes VELCRO brand hook and loop fasteners, or generic hook and loop fasteners. Structurally, it is about twenty nine inches long and has a small hook-carrying section 82 and a longer loop-carrying section 84 that releasably engage one another in the well-known way. The drawings are reversed and should show section 82 as the loop-carrying section and section 84 as the hook-carrying section. The medial part of the strap, which is uncovered by said hooks and loops, is denoted 86. Note slot 88 formed in said medial part near the hook-carrying part 82. This slot bifurcates the strap into parts 90, 92 which are spread apart as depicted in FIGS. 7 and 9 into upper and lower bite block-engaging means. Thus, it should be understood that the length of slot 88 is slightly greater than the collective width of bite block 60, and that parts 90, 92 reconverge just beyond the side edges of side parts 64, 66. This enables facile attachment of the novel strap 80 and further assures firm holding of the bite block 60.

The second embodiment of the invention is shipped to the final user with strap 80 already installed. Thus, all the final user need do is insert mouthpiece 68 into the patient's mouth and fasten strap 80 by placing hook part 82 into overlying relation to loop part 84 as required. Note that hook-covered part 82 is adjacent side part 64 or 66 as mentioned earlier because it is immediately adjacent slot 88. This ensures that the medical personnel attaching strap 80 will never have to move a patient's head to perform the attachment procedure because side part 64 or 66 and hence hook (or loop) carrying part 82 or 84 will always be accessible; this is due to the fact that side parts 64, 66 overlie the patient's face near the corner of the mouth, and at least one corner of the mouth will always be accessible, even when the patient's head is turned to the side. All prior art bite blocks, including the novel bite block of the first embodiment, require displacement of the patient's head to enable attachment of a first end of a strap to a first end of the bite block and a second end of the strap to a second end of the bite block, i.e., strap attachment requires access to both sides of the bite block, and access to one side of the patient's face will almost always be blocked by a pillow. The second embodiment disclosed herein completely eliminates that problem and thus eliminates the need to move a patient's head when attaching strap 80.

The use of VELCRO brand, or generic hook and loop fasteners, enables health care personnel to manipulate the strap with a gloved hand. Moreover, the stretchability of the strap increases its comfort to the patient and enhances the utility of the invention as a whole.

The numerous features of both embodiments of this invention were heretofore unknown.

This invention is clearly new and useful. Moreover, it was not obvious to those of ordinary skill in this art at the time it was made, in view of the prior art considered as a whole as required by law.

It will thus be seen that the objects set forth above, and those made apparent from the foregoing description, are efficiently attained and since certain changes may be made in the above construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A bite block, comprising:

a base member and a pair of side members connected to opposite sides of said base member;

a mouthpiece formed integrally with said base member and said side members;

said base member and side members having a common height that is about twice as great as the collective width of said base and side members;

a common gentle curve being formed in said base member and said side members so that said base and side members conform, senerally, to the contour of a human face when said base member is disposed in overlying relation to a person's mouth;

said base member having an upper end, a lower end, and a medial part;

each of said side members having an upper end, a lower end, and a medial part;

said side members and said base member being integrally formed with said mouthpiece at their respective medial parts and said side members being spaced apart from said base member by a predetermined distance at their respective upper and lower ends;

said spacing at said upper ends of said base member and said side members forming a pair of laterally spaced apart upper slots and said spacing at said lower ends forming a pair of laterally spaced apart lower slots;

an elongate strap for retaining said bite block in position when opposite ends of said strap are secured to one another;

said elongate strap having an elongate slot formed therein at a preselected location along its length, said slot being parallel to a longitudinal axis of said strap said slot enabling a first part of said strap to weave through said upper slots and a second part of said strap to weave through said lower slots.

2. The bite block of claim 1, further comprising a strap-retention lug formed on opposite sides of said base member upper end and lower end.

3. The bite block of claim 2, further comprising a tooth-retaining ridge formed on a top surface and a bottom surface of said mouthpiece, said ridge having a leading end that extends to a leading end of said mouthpiece and a ramp being formed in said leading end of said ridge to facilitate introduction of said mouthpiece into a patient's mouth.

4. The bite block of claim 3, wherein said strap is formed of an elastomeric material.

5. The bite block of claim 4, wherein said opposite ends of said strap are secured to one another by hook and loop fastening material so that said strap may be manipulated by a gloved hand.

* * * * *